(12) United States Patent
Terasawa et al.

(10) Patent No.: US 7,911,600 B2
(45) Date of Patent: Mar. 22, 2011

(54) APPARATUS AND A METHOD FOR INSPECTION OF A MASK BLANK, A METHOD FOR MANUFACTURING A REFLECTIVE EXPOSURE MASK, A METHOD FOR REFLECTIVE EXPOSURE, AND A METHOD FOR MANUFACTURING SEMICONDUCTOR INTEGRATED CIRCUITS

(75) Inventors: Tsuneo Terasawa, Tokyo (JP); Toshihiko Tanaka, Tokyo (JP); Tatsuya Aota, Hyogo (JP)

(73) Assignee: Renesas Electronics Corporation, Kanagawa (JP)

( * ) Notice: Subject to any disclaimer, the term of this patent is extended or adjusted under 35 U.S.C. 154(b) by 224 days.

(21) Appl. No.: 12/241,614

(22) Filed: Sep. 30, 2008

(65) Prior Publication Data
US 2009/0091752 A1  Apr. 9, 2009

(30) Foreign Application Priority Data
Oct. 4, 2007  (JP) ................................. 2007-260796

(51) Int. Cl.
*G01N 21/00* (2006.01)
(52) U.S. Cl. ................. 356/237.5; 356/237.1; 356/237.2
(58) Field of Classification Search ..... 356/237.1–237.5
See application file for complete search history.

(56) References Cited

U.S. PATENT DOCUMENTS

| 6,617,603 | B2 |  | 9/2003 | Ishiguro et al. |
| 6,657,714 | B2 | * | 12/2003 | Almogy et al. ............ 356/237.3 |
| 6,954,266 | B2 |  | 10/2005 | Tomie |
| 7,315,366 | B2 | * | 1/2008 | Hamamatsu et al. ...... 356/237.2 |
| 7,463,350 | B2 | * | 12/2008 | Nishiyama et al. ........ 356/237.4 |
| 7,511,806 | B2 | * | 3/2009 | Hamamatsu et al. ...... 356/237.2 |
| 2004/0057107 | A1 |  | 3/2004 | Yun et al. |
| 2007/0121106 | A1 | * | 5/2007 | Shibata et al. ............ 356/237.2 |
| 2009/0059215 | A1 | * | 3/2009 | Mehanian et al. ......... 356/237.2 |

FOREIGN PATENT DOCUMENTS

| JP | 6-349715 | 12/1994 |
| JP | 11-354404 | 12/1999 |
| JP | 2001-174415 | 6/2001 |
| JP | 2002-333313 | 11/2002 |
| JP | 2003-114200 | 4/2003 |

* cited by examiner

*Primary Examiner* — Michael P Stafira
(74) *Attorney, Agent, or Firm* — McDermott Will & Emery LLP

(57) ABSTRACT

The mask blank inspection apparatus is constituted of a stage for mounting a reflective mask blank thereon, a light source for generating inspection light, a mirror serving as an illuminating optics, an imaging optical system, a beam splitter, two two-dimensional array sensors, signal storage units, an image processing unit, a main control unit for controlling operation of the whole apparatus, the first sensor being located at a position which is displaced by a predetermined distance from the focal plane of a first light beam, the second sensor being located at a position which is displaced by a predetermined distance from the focal plane of a second light beam along a opposite direction, whereby accurately and conveniently inspecting presence/absence and types of defects in reflective mask blank.

11 Claims, 10 Drawing Sheets

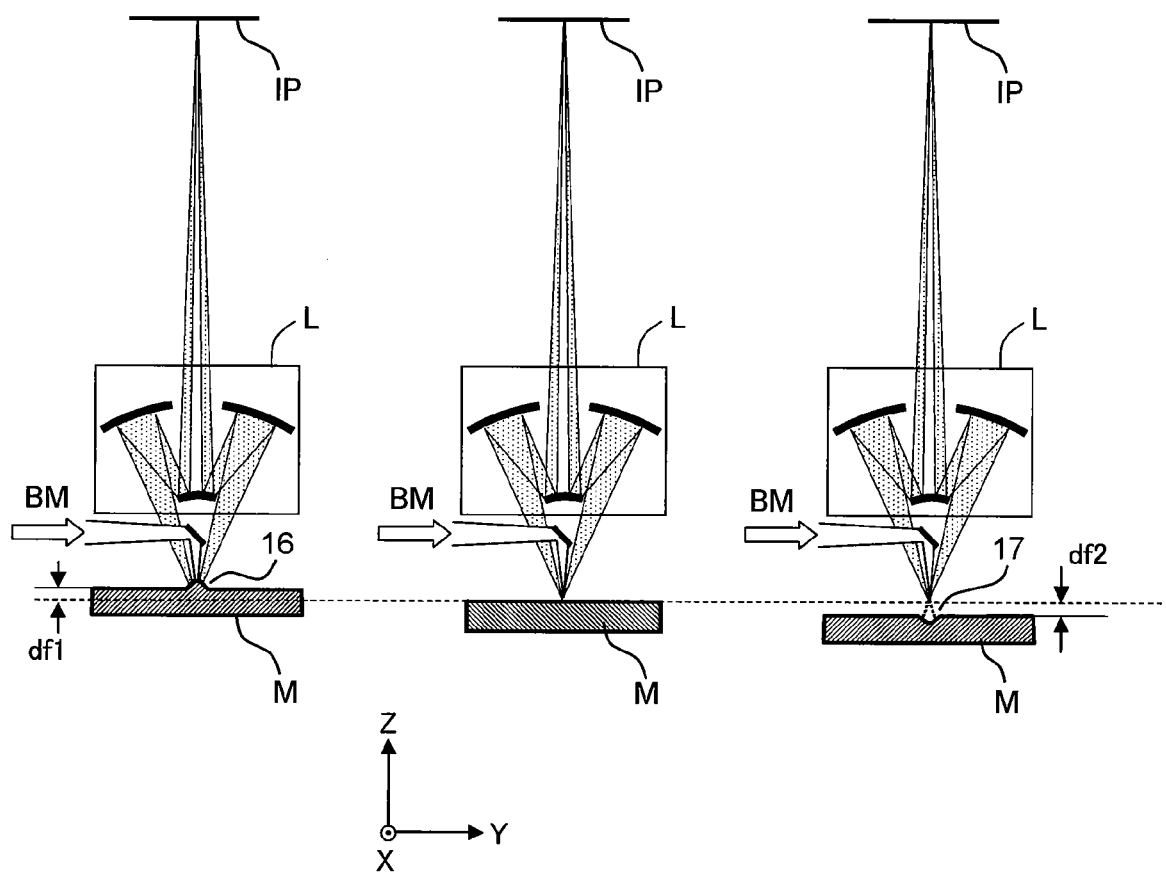

APPARATUS AND A METHOD FOR INSPECTION OF A MASK BLANK, A METHOD FOR MANUFACTURING A REFLECTIVE EXPOSURE MASK, A METHOD FOR REFLECTIVE EXPOSURE, AND A METHOD FOR MANUFACTURING SEMICONDUCTOR INTEGRATED CIRCUITS

BACKGROUND OF THE INVENTION

1. Field of the Invention

The present invention relates to an apparatus and a method for inspection of a mask blank suitable for, for example, EUVL (Extreme Ultra Violet Lithography) using extreme ultraviolet radiation with a wavelength of about 13.5 nm. The invention also relates to a method for manufacturing a reflective exposure mask, a method for reflective exposure, as well as a method for manufacturing semiconductor integrated circuits.

2. Description of the Related Art

Semiconductor devices, such as semiconductor integrated circuits, are mass produced by repetitively using a optical lithography process in which a mask, i.e., a master having a circuit pattern drawn thereon, is irradiated with exposure light so that the pattern is transferred onto a semiconductor substrate (hereinafter, referred to as "wafer") via reduction projection optics.

In recent years, as scale-down of semiconductor devices have been progressing, there are discussed methods for enhancing the resolution by further shortening the exposure wavelength of optical lithography. While ArF lithography using argon fluoride excimer laser light having a wavelength of 193 nm has been developed so far, EUVL having a far shorter wavelength of 13.5 nm has been being developed.

In the EUV wavelength region, since transmissive masks cannot be used in terms of light absorption by substances, multilayered reflective substrates, which can effect reflection due to a multilayer film of, e.g., Mo (molybdenum) and Si (silicon) (i.e., Bragg reflection), are employed for mask blanks for EUVL. The multilayer-film reflection is a reflection exploiting a type of interference. In a mask for EUVL, an absorber pattern is formed on a multilayer coated mask blank which has a multilayer film of, e.g., Mo and Si deposited on quartz glass or low thermal expansion glass substrate.

In EUVL, because of reflective masks using Bragg reflection and an extreme short exposure wavelength of 13.5 nm, occurrence of even slight height irregularities as small as a fraction of the exposure wavelength may cause local differences in reflectivity due to those height irregularities, resulting in defects during transfer processes. Accordingly, masks for EUVL largely are different in quality of defect transfer from conventional transmission masks.

For the mask blank defect inspection in the preceding step prior to formation of an absorber pattern, two methods are available: one is a method in which a mask blank is obliquely irradiated with laser light to detect any foreign object from its diffused reflection light, and the other is an at-wavelength defect inspection method in which EUV light of the same wavelength as that for use in makes pattern exposure is used for defect detection. The latter method further includes a method employing dark field images (see, e.g., JP-2003-114200 A), an X-ray microscope method employing the bright field images (see, e.g., JP-6-349715 A (1994)), and a dark-field bright-field combinational method in which dark field images are used for defect detection and then defect identification is performed in the bright field system using a Fresnel zone plate (see, e.g., US 2004/0057107 A).

Incidentally, for conventional transmissive mask blank inspections, two methods are known: a mask blank is obliquely irradiated with laser light to detect any foreign object from its diffused reflection light in one method, and a bright field image (microscopic image) is detected in another method. Modifications of the latter method is to discriminate between convex defects and concave defects based on asymmetries of detected image signals (see, e.g., JP-2001-174415 A, and JP-2002-333313 A).

Further, yet another method is disclosed in which a peelable pattern is formed on a multilayer coated mask blank, and then actual pattern is transferred therewith, and then the pattern is examined to inspect multilayer-film defects (see, e.g., JP-11-354404 A (1999)).

However, in JP-2003-114200 A, the dark field detection method employing EUV light is highly sensitive in detection and excellent in detection performance for phase defects due to irregularities of multilayer film, but incapable of discriminating between concave and convex defects simultaneously.

Also, in JP-6-349715 A (1994), the X-ray microscope method employing the bright field examines only the reflection ratio of the multilayer film, hence, all of defects causing changes in phase cannot be detected.

Also, in US 2004/0057107 A, the method, that is an exposure wavelength inspection serving as both a bright field inspection and a dark field inspection, involves more complicated inspection equipment and, although being a high-speed dark field inspection, yet is not highly sensitive in detection.

Also, as in JP-2001-174415 A, and JP-2002-333313 A, the method employing laser is insufficient in sensitivity because defects to be detected are too small as compared with the inspection wavelength. Moreover, the method can detect concave and convex defects residing only on the surface of the multilayer film, but cannot capture defects which reside inside the multilayer film and may cause abnormalities of EUV light reflection.

Further, in JP-11-354404 A (1999), the method in which a peelable pattern is formed on the multilayer coated mask blank, and then actual pattern is transferred therewith, and then the pattern is examined to detect multilayer-film defects, can detect phase defects, but requires a further step of actual transfer of pattern transfer, resulting in cumbersome inspection.

In any of the inspection methods as described above, in case any defect that is hard to repair is detected, even if the defect is of minute size, the mask blank involved is regarded as a defective, being put into disposal.

SUMMARY OF THE INVENTION

An object of the present invention is to provide an apparatus and a method for inspection of a mask blank, which can accurately and conveniently inspect presence/absence and types of defects in reflective mask blank.

Further, an object of the invention is to provide a method for manufacturing a reflective exposure mask, which can manufacture a reflective exposure mask with high reliability and yield even if presence of any defect has been proved by the above-described inspection method.

Furthermore, an object of the invention is to provide a method for reflective exposure using such a reflective exposure mask as obtained by the above-described manufacturing method.

Further, an object of the invention is to provide a method for manufacturing semiconductor integrated circuits using the above-described method for reflective exposure.

According to an embodiment of the invention, a reflective mask blank to be inspected is irradiated with inspection light to illuminate a target region, followed by collecting scattered light other than specularly reflected light out of light reflected from the target region by means of a dark-field imaging optics. The collected light is divided into a first light beam and a second light beam by an optical branching element.

A first image sensor is located at a position displaced by a predetermined distance from a focal plane of the first light beam along the light traveling direction. The second image sensor is located at a position displaced by a predetermined distance from a focal plane of the second light beam along a direction opposite to the light traveling direction. These first and second image sensors can measure intensity distributions of respective inspection images formed by the first and the second light beams, respectively. Signals derived from the first and the second image sensors are fed to an image processing unit, where presence or absence of any defects in the mask blank is determined.

The optical branching element is preferably composed of a multilayer film, a transmissive diffraction grating or a reflective diffraction grating.

The first and the second image sensors are preferably image sensors capable of TDI (Time Delayed Integration) operations in synchronization with continuous movement of a stage.

The inspection light preferably has a wavelength equal to that used for mask pattern exposure, being, e.g., extreme ultraviolet light having wavelengths of 10 nm to 15 nm.

When determining presence or absence of defects, convex defects and concave defects of the surface configuration are preferably discriminated by comparing signals from the first and the second image sensors with preset first and second threshold values, respectively.

Further, in the case where a reflective exposure mask is manufactured with an absorber pattern formed on a reflective mask blank, the mask blank is inspected for any defects as described above to store positional information of the defects in advance. Subsequently, based on the stored defect positional information, a relative position between an absorber pattern mask and the mask blank for defining a forming position of the absorber pattern is determined. In this process, the absorber pattern may be positioned in such a manner, for example, that the absorber pattern can conceal the defects. Then, based on the determined relative position, the absorber pattern is formed on the mask blank.

After the mask obtained in this way is mounted on a reflective exposure apparatus, the absorber pattern can be projected in a reduced size onto a semiconductor substrate. Further, by using such a reflective exposure method, an integrated circuit pattern can be formed on the semiconductor substrate to manufacture semiconductor integrated circuits.

According to this embodiment, presence/absence and types of defects in a reflective mask blank can be accurately and conveniently inspected, thereby allowing factors of defect generation to be analyzed. Further, by utilizing the obtained defect positional information, the absorber pattern can be formed on the reflective mask blank so as to avoid any effects of defects, thereby improving the yield of the reflective exposure mask.

BRIEF DESCRIPTION OF THE DRAWINGS

FIG. 3A is an explanatory view showing a detection state of the mask blank containing the convex defect, FIG. 3B is an explanatory view showing a detection state of the defect-free mask blank, and FIG. 3C is an explanatory view showing a detection state of the mask blank containing the concave defect;

DETAILED DESCRIPTION OF THE PREFERRED EMBODIMENTS

This application is based on the application No. 2007-260796 filed on Oct. 4, 2007 in Japan, the disclosure of which is incorporated herein by reference.

Hereinafter, preferred embodiments will be described with reference to drawings.

Embodiment 1

Figure 1:
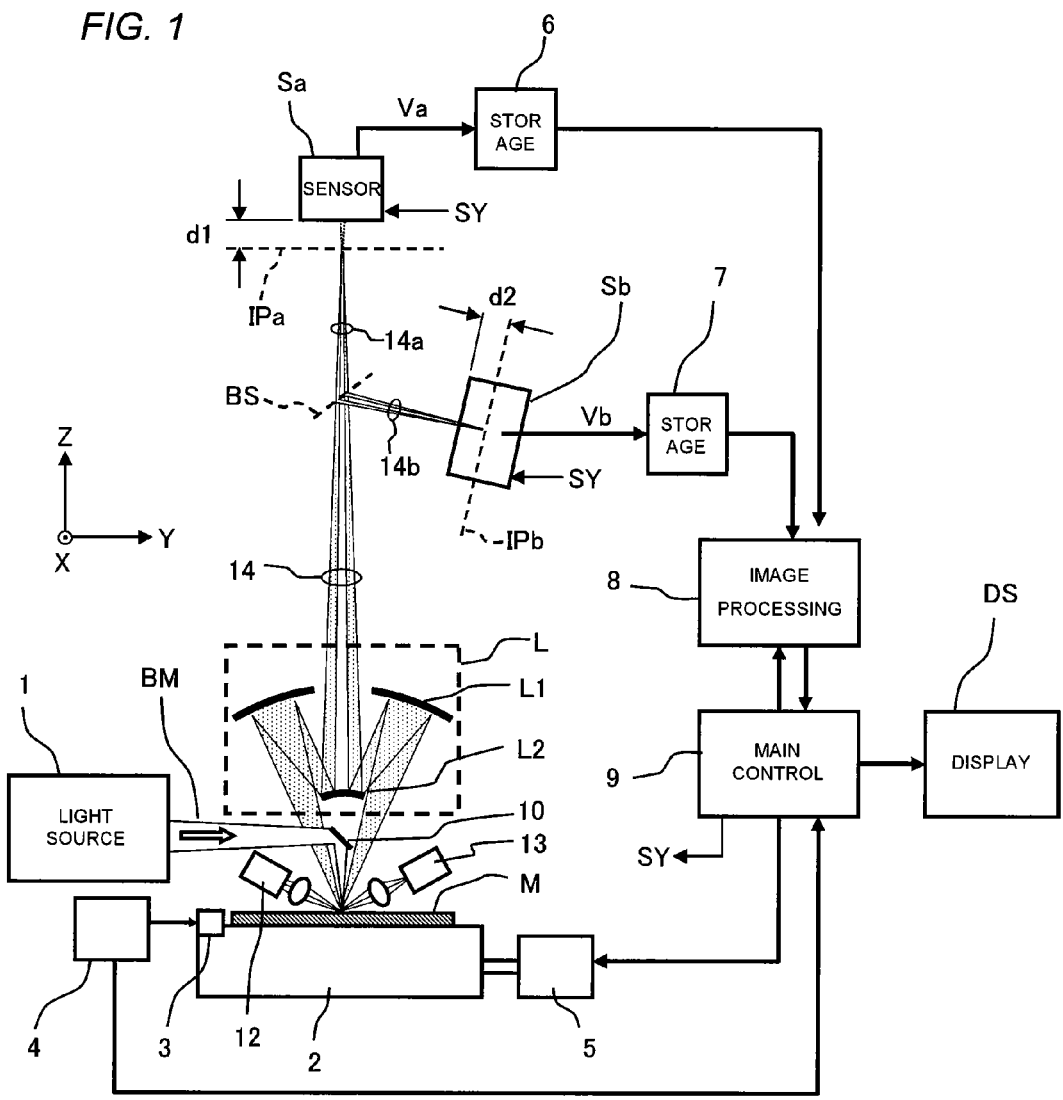
FIG. 1 is a configurative view showing an example of the mask blank inspection apparatus according to the present invention.

FIG. 1 is a configurative view showing an example of a mask blank inspection apparatus according to the present invention. The mask blank inspection apparatus is constituted of a stage 2 for mounting a reflective mask blank M thereon, a light source 1 for generating inspection light BM, a mirror 10 serving as an illuminating optics, an imaging optical system L, a beam splitter BS, two two-dimensional (2D) array sensors Sa and Sb, signal storage units 6 and 7, an image processing unit 8, a main control unit 9 for controlling operation of the whole apparatus. For easier understanding, it is assumed here that the stage surface is an XY plane and the direction normal to the stage surface is a Z axis.

The mask blank M, as shown in FIG. 2, has a multilayer film ML on a mask substrate MS. The multilayer film ML is formed of Si (silicon) and Mo (molybdenum) alternately stacked to achieve a sufficient reflectance for exposure light of a wavelength (e.g., 13.5 nm). The mask substrate MS is formed of a low thermal expansion material, such as quartz glass. An absorber pattern having a desired shape of pattern is formed on the multilayer film ML, resulting a reflective exposure mask.

Reverting to FIG. 1, the light source 1 is configured of an EUV light source for generating inspection light BM containing the same wavelength as the exposure light. The mirror 10, which may be a concave mirror or a plane mirror, condenses the inspection light BM supplied from the light source 1 into a spot to illuminate a target region on the mask blank M. The incident direction of the inspection light BM is set to generally coincide with the normal direction of the mask blank M.

The imaging optical system L includes a concave mirror L1 and a convex mirror L2 to form a Schwarzschild optics in which an exit opening is located at a center of the concave mirror L1. As to the light reflected from the target region, mirror reflected light that goes along a specular reflection direction and its proximities is intercepted by the convex mirror L2, thus providing a dark field optical system. Meanwhile, scattered light that is incident on the concave mirror L1 is magnified and projected according to a magnifying power combined by the concave mirror L1 and the convex mirror L2, and then outputted along Z direction through the exit opening of the concave mirror L1. The imaging optical system L may be designed with, for example, the numerical aperture of the concave mirror L1 being 0.2, the center light-intercepting numerical aperture of the convex mirror L2 being 0.1, and the combined magnification being 26.

In such a dark field optical system as noted above, in a case where no defect is present on the mask blank M, no scattered light is generated while only specularly reflected light remains, which cannot be captured by the imaging optical system L, nor does go incident on the 2D array sensors Sa and Sb. In another case where some defects are present on the mask blank M, scattered light is generated, followed by being captured by the imaging optical system L and then going incident on the 2D array sensors Sa and Sb. Therefore, inspection with a higher S/N ratio can be performed.

The beam splitter BS, which is placed on the exit side of the imaging optical system L, divides an output light beam 14 into two light beams 14a and 14b to form a focal plane IPa of the light beam 14a and a focal plane IPb of the light beam 14b, respectively. In this embodiment, the beam splitter BS is formed of a multilayer film composed of several pairs of Si and Mo, and so designed as to have a transmissivity of about 30% and a reflectivity of about 30% for EUV light.

The 2D array sensor Sa is located for detecting a positively defocused image, at a position which is displaced by a predetermined distance d1 from the focal plane IPa of the light beam 14a along the light traveling direction. On the other hand, the 2D array sensor Sb is located for detecting a negatively defocused image, at a position which is displaced by a predetermined distance d2 from the focal plane IPb of the light beam 14b along a direction opposite to the light traveling direction.

The 2D array sensors Sa and Sb may be configured of, for example, a CCD (Charge Coupled Device) having a plurality of detection pixels, thus serving to convert each distribution of light intensity on each light-receiving surface into electric signals Va and Vb, respectively. Alternatively, the 2D array sensors Sa and Sb may also be configured of image sensors which are capable of TDI (Time Delayed Integration) operations in synchronization with continuous movement of the stage 2 using a synchronous signal SY supplied from a main control unit 9, thereby achieving reduction of noise and enhancement of sensitivity using signal integration.

The signal storage units 6 and 7 can temporarily store the electric signals Va and Vb outputted from the 2D array sensors Sa and Sb to perform noise elimination process as well as initialization process of pixel numbers that define positions of detection signals. The image processing unit 8 examines signals processed by the signal storage units 6 and 7 to determine presence/absence and type of defect residing in the mask blank M. A determination result of the image processing unit 8 is sent via the main control unit 9 to a display unit DS, such as a display monitor, which can display defect information including the presence or absence, number, size, positions and so on of defects.

The stage 2 can be moved stepwise or continuously in X and Y directions by a stage drive unit 5 based on a command from the main control unit 9. Target mirrors 3 are fixed onto the stage 2 to accurately measure X and Y displacements of the stage 2 using laser interferometers 4. Measured positional information on the stage 2 is transmitted to the main control unit 9.

Also, a height (Z position) of the stage 2 can be measured by obliquely illuminating the surface of the mask blank M with a laser light source 12 and then detecting its reflected light using a sensor 13. Measured height information on the stage 2 is transmitted to the main control unit 9.

The stage 2 may incorporate a height adjustment mechanism (not shown), thereby enabling focusing control for the inspection light BM, so that even when the stage 2 moves in X and Y directions, the height of the stage 2 can be adjusted to keep the position of reflected light received on the sensor 13 constant.

The stage 2 also may incorporate a mechanism for adjusting both tilt angles about X and Y axes (not shown). Placement of a plurality of the above-described laser height measuring instruments enables compensation of tilting error so that the surface of the mask blank M can be always kept parallel to XY plane even when the stage 2 moves in X and Y directions.

Also, although not shown, an alignment scope for detecting a fiducial mark formed on the mask blank M is provided in proximity to the stage 2.

Figure 2A:
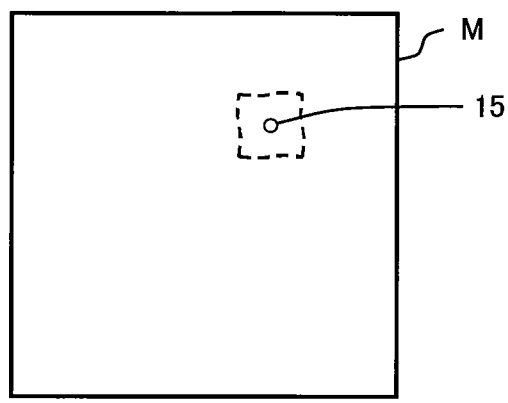
FIG. 2A is a plain view showing the whole reflective mask blank.
Figure 2B:
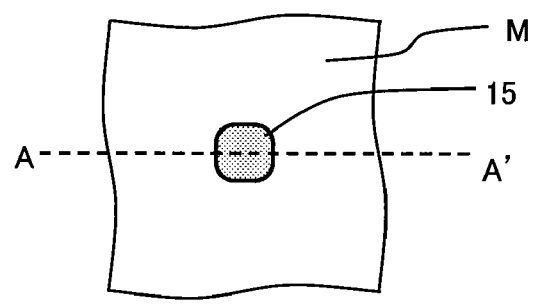
FIG. 2B is an enlarged view including a defect.
Figure 2C:
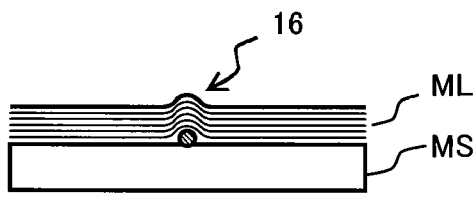
FIG. 2C is a cross-sectional view of the line A-A' showing an aspect of a convex defect.
Figure 2D:
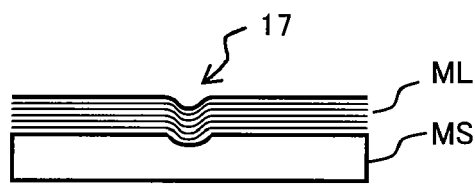
FIG. 2D is a cross-sectional view of the line A-A' showing an aspect of a concave defect.

FIG. 2A is a plain view showing the whole reflective mask blank M, and FIG. 2B is an enlarged view including a defect 15. FIGS. 2C and 2D are cross-sectional views taken along the line A-A', where FIG. 2C shows an aspect of a convex defect and FIG. 2D shows an aspect of a concave defect.

The mask blank M is designed so that a multilayer film ML in which Si (silicon) and Mo (molybdenum) are alternately stacked is formed on the mask substrate MS to achieve a sufficient reflectance for the exposure light of a wavelength (e.g., 13.5 nm).

During formation of the multilayer film ML, if fine particles, such as foreign matters, are present on the mask substrate MS, the multilayer film ML is affected by those particles so that the surface of the multilayer film ML is likely to have a convex shape, resulting in a convex phase defect 16, as shown in FIG. 2C. Conversely, if minute dents or pits are present on the surface of the mask substrate MS, the surface of the multilayer film ML is likely to have a concave shape, resulting in a concave phase defect 17, as shown in FIG. 2D.

FIG. 3A is an explanatory view showing a detecting state with an intensity of defect detection signal of the mask blank M containing the convex defect 16 being maximum. FIG. 3B is an explanatory view showing a state with the defect-free mask blank M being placed at a focused position of the detection optical system. FIG. 3C is an explanatory view showing a detecting state with an intensity of defect detection signal of the mask blank M containing the concave defect 17 being maximum. For easier understanding, here is described by way of an example in which the beam splitter BS is omitted while an array sensor is placed at a focal plane IP of the imaging optical system L for detecting an intensity of light.

The convex defect 16 has a slight height as small as 6 nm. The concave defect 17 has a slight depth as small as 6 nm. In either case, with the mask blank M being vertically irradiated with the inspection light BM, focusing control for adjusting the height of the mask blank M is performed so that the intensity of light becomes maximum at the focal plane IP, wherein the resulting height is regarded as an optimum focus position.

In comparison with such a focus position resulting from focusing control for the defect-free mask blank M as shown in FIG. 3B, if such a convex defect 16 as shown in FIG. 3A is present, the convex defect 16 acts like a convex mirror, causing the focus position to be shifted in such a direction that the optical path length is shortened by a distance df1. On the other hand, if such a concave defect 17 as shown in FIG. 3C is present, the concave defect 17 acts like a concave mirror, causing the focus position to be shifted in such a direction that the optical path length is lengthened by a distance df2.

Figure 4:
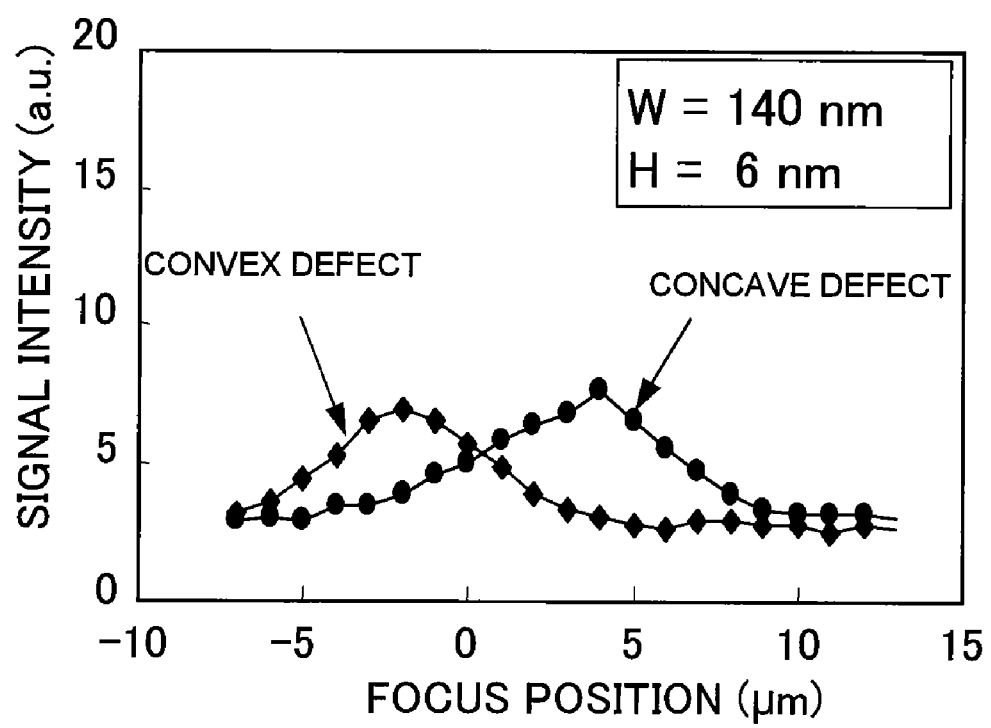
FIG. 4 is a graph showing a relationship between signal intensity at the focal plane and focus position of the mask blank.

FIG. 4 is a graph showing a relationship between signal intensity at the focal plane IP and focus position of the mask blank. The vertical axis shows the signal intensity of a detected dark field image, and the horizontal axis shows the focus position (i.e., focus level), wherein the focus position is getting larger while the position of the mask blank M goes farther away from the imaging optical system L. Please note that the focus position of the defect-free mask blank M is 0. Exemplified here are cases of a convex defect with a diameter W=140 nm and a height H=6 nm as well as a concave defect with a diameter W=140 nm and a depth H=6 nm.

Referring to FIG. 4, in a case of a convex defect being present, the focus position resulting from focusing control is shifted in such a direction as to be closer to the imaging optical system L. In another case of a concave defect being present, on the other hand, the focus position resulting from focusing control is shifted in such a direction as to be farther from the imaging optical system L.

In this embodiment, as shown in FIG. 1, the light beam 14 outputted from the imaging optical system L is branching into two light beams 14a and 14b through the beam splitter BS, and their images can be simultaneously measured using the two 2D array sensors Sa and Sb with different amount of defocuses.

Given a magnifying power MAG of the imaging optical system L, it is preferable to set a distance $d1=MAG^2 \times df1$ between the light receiving surface of the 2D array sensor Sa and the focal plane IPa of the light beam 14a, and a distance $d2=MAG^2 \times df2$ between the light receiving surface of the 2D array sensor Sb and the focal plane IPb of the light beam 14b.

Incidentally, in the configuration shown in FIG. 1, it is preferable that the beam splitter BS can be moved detachably from the focusing optical path as required. In other words, it is also achievable to built up another configuration for the dark field detection apparatus that can capture a detecting signal using only a single 2D array sensor Sa. In this case, preferably, the light receiving surface of the sensor Sa is generally coincident with the focal plane IPa of the imaging optical system L, thereby increasing the intensity of inspection light approximately threefold.

Next, a method for inspection of a mask blank according to this embodiment is described in detail with reference to flowcharts shown in FIGS. 5 and 6.

Figure 5:
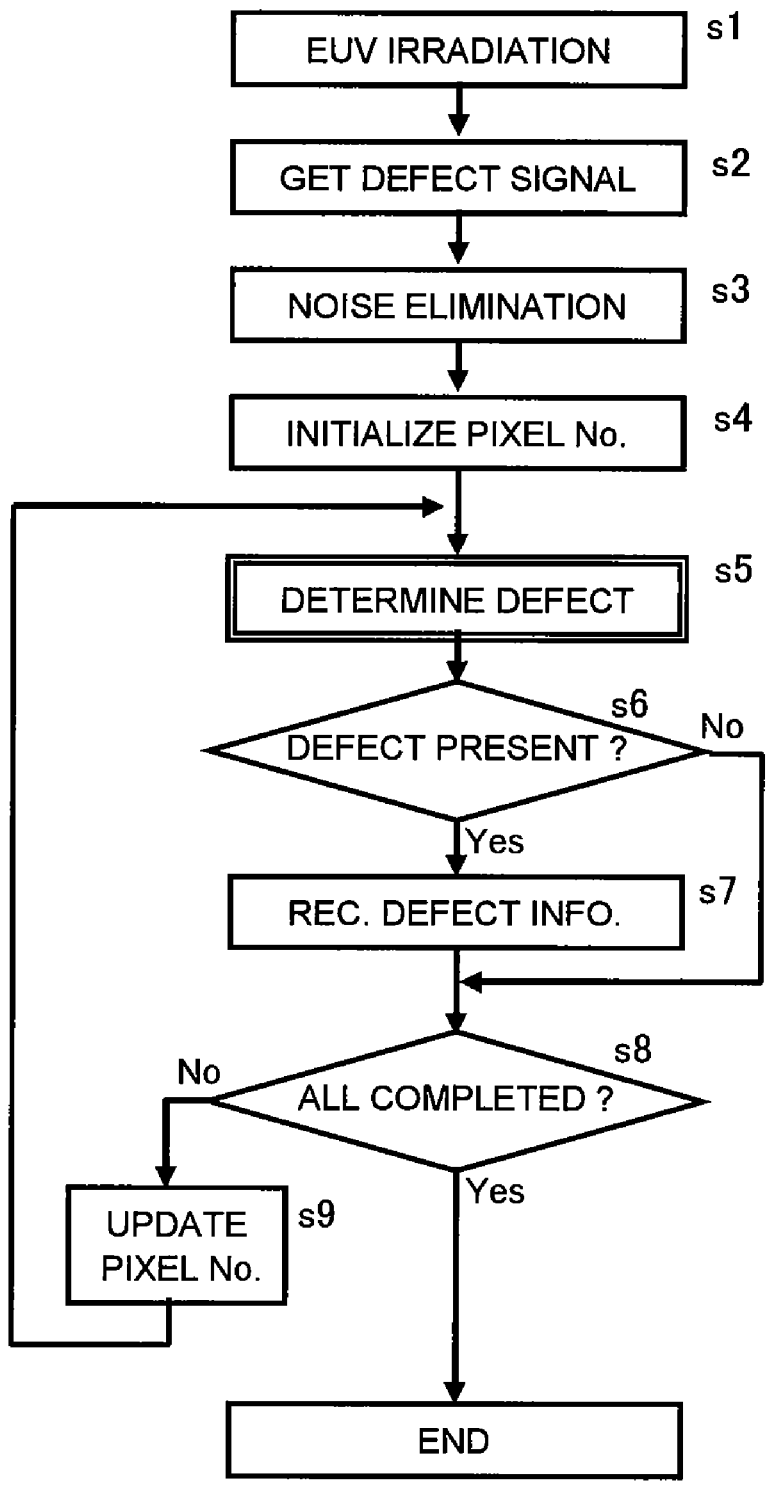
FIG. 5 is a flowchart showing a method for inspection of a mask blank according to this embodiment.

First, at step s1 of FIG. 5, as shown in FIG. 1, the reflective mask blank M having the multilayer film ML is mounted on the stage 2, and then positioned at a desired XY position using the stage drive unit 5, followed by irradiating it with the inspection light BM to illuminate the target region of the mask blank M.

Next, at step s2, the light beam 14 outputted from the imaging optical system L branches into two light beams 14a and 14b through the beam splitter BS, and then respective detection signals thereof are acquired using the 2D array sensors Sa and Sb. These detection signals are captured into the signal storage units 6 and 7. Subsequently, the signals are subjected to noise elimination process (step s3), and then initialization process for pixel numbers that define positions of detection signals (step s4).

Next, at step s5, the image processing unit 8 performs determination process as to presence or absence of defects. Subsequently, at step s6, if it is determined that a defect is present, going to step s7, defect information including presence or absence, number, size, position and so on of defects is recorded in a data management system.

Next, at step s8, it is judged whether or not the processing for all pixels has been completed, where if there is any pixel left to be processed, the pixel number is updated (step s9), and then jumping to step s5 to repeat again the determination process for presence or absence of defects.

Figure 6:
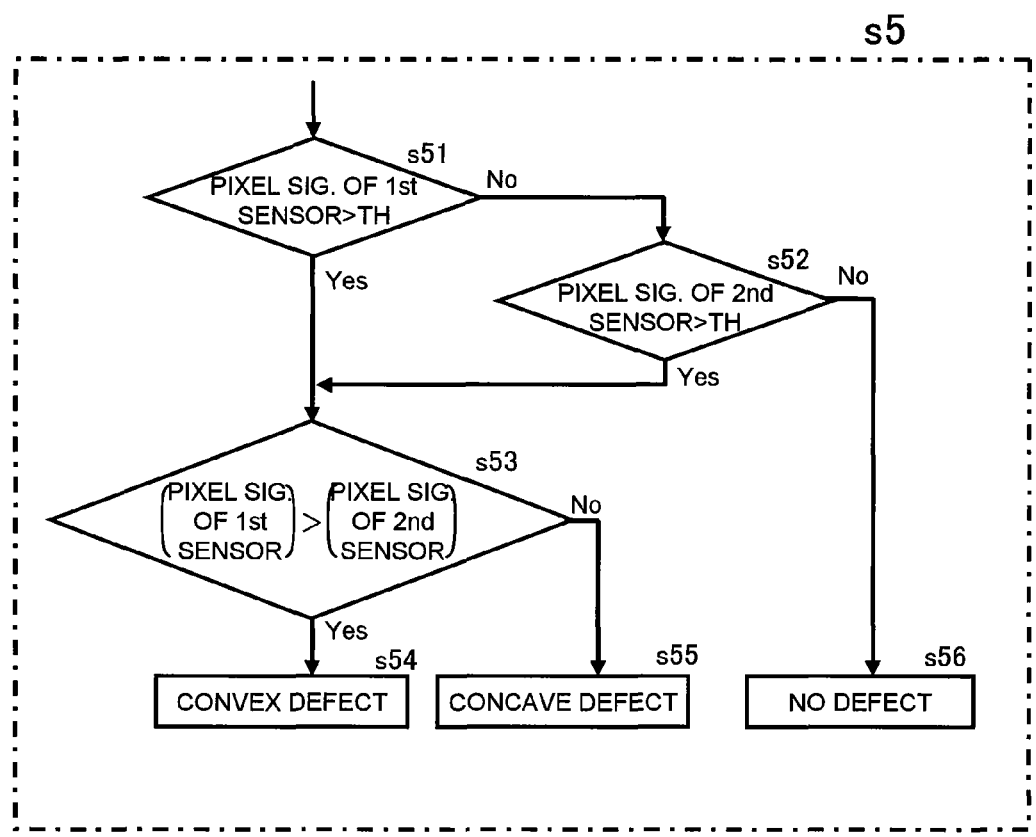
FIG. 6 is a flowchart showing details of the determination process as to presence or absence of defects in step s5 of FIG. 5.

FIG. 6 is a flowchart showing details of the determination process as to presence or absence of defects in step s5. If a defect is present in the mask blank M, there is an increased signal level in any pixel of the 2D array sensors Sa and Sb corresponding to the position of defect. Since inspection signals of one position are captured into the two 2D array sensors Sa and Sb via the beam splitter BS, the presence or absence of any defect can be determined by judging whether or not inspection signal levels of the two sensors exceed a preset threshold value TH.

More specifically, first at step s51, a signal of a specified pixel of the first 2D array sensor Sa is compared with the preset threshold value TH. If the pixel signal level is not higher than the threshold value TH, then at step s52 a signal of a corresponding pixel of the second 2D array sensor Sb is compared with the threshold value TH. As a result of the comparison, if the signal level of any of the pixels is not higher than the threshold value TH, then it can be determined that there is no defect (step s56).

On the other hand, if the signal level of pixel of the first 2D array sensor Sa or the signal level of pixel of the second 2D array sensor Sb is higher than the threshold value TH, then in turn at step s53 a signal of a specified pixel of the first 2D array sensor Sa is compared with a signal of a specified pixel of the second 2D array sensor Sb. If the former signal is higher in level than the latter, then it can be determined that there is a convex defect (step s54). If the former is not higher in level than the latter, then it can be determined that there is a concave defect (step s55).

Please note that the threshold value TH for the defect determination is preferably set so as not to be affected by a background level of the detection signal originating from noise due to optical systems or electrical noise of, e.g., the 2D array sensors, affection of which can be estimated in advance.

Further, the 2D array sensors Sa and Sb are preferably calibrated so that the outputs of the same level can be obtained upon reception of light of the same level. In this case, if the light beams 14a and 14b branching via the beam splitter BS differ in intensity from each other, sensitivities of the 2D array sensors Sa and Sb are preferably calibrated in correspondence to ratio of intensities of the light beams 14a and 14b, thereby obtaining the outputs of the same level.

Figure 7A:
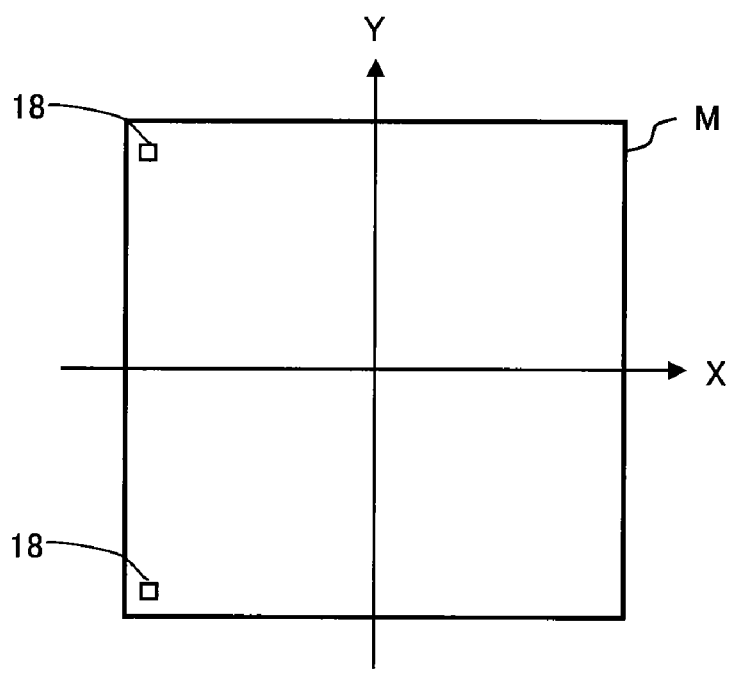
FIG. 7A is a plain view showing the whole mask blank M on which fiducial marks are formed.
Figure 7B:
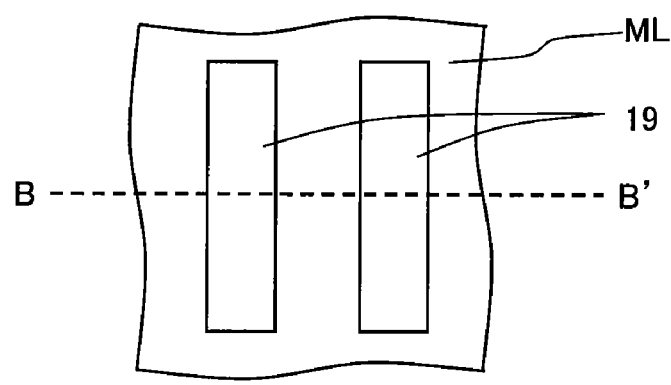
FIG. 7B is an enlarged view of a fiducial mark.
Figure 7C:
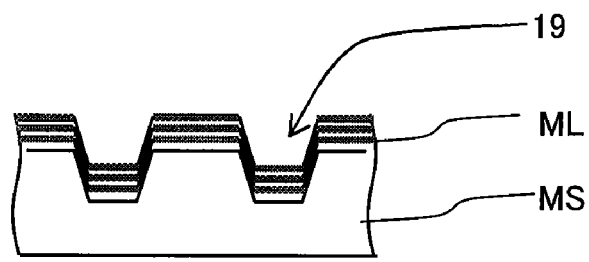
FIG. 7C is a cross-sectional view taken along the line B-B' of FIG. 7B.

FIG. 7A is a plain view showing the whole mask blank M on which fiducial marks 18 are formed. FIG. 7B is an enlarged view of the fiducial mark 18, and FIG. 7C is a cross-sectional view taken along the line B-B' of FIG. 7B.

In general, the mask blank M has a rectangular shape, with the fiducial marks 18 provided in advance at proximities to neighboring two of four corners. These fiducial marks 18 can act as reference points for forming absorber patterns on the multilayer film ML. During inspection of the mask blank M, reference coordinates of the mask blank M can be precisely determined by measuring the fiducial marks using an alignment scope (not shown).

In part of the surface of an ultra smooth substrate constituting the mask blank M, fine-width recesses 19 are formed in advance by FIB (Focused Ion Beam) or the like. The fiducial marks 18 are formed at positions corresponding to the recesses 19 by depositing the multilayer film ML so as to cover the recesses 19. Exemplified here is a case where a pair of recesses 19 constitute a single fiducial mark 18.

When observing with EUV light, the recesses 19 can be recognized as pattern portions involving large change of phase. Therefore, with the fiducial marks 18 used as coordinate references on the mask blank M, the position of a detected defect can be defined by relative coordinates on the basis of the fiducial marks 18.

The fiducial marks 18 can facilitate pattern detection from the reflected light even when illuminated with electron beams, ultraviolet or visible light. As a result, for example, in forming an absorber pattern using an electron beam, the fiducial marks 18 as well as defects can be detected using the electron beam.

The fiducial marks 18 are preferably arranged at two or more positions for the single mask blank M. Arrangement of the fiducial marks 18 at two or more positions enables rotating deviation of the mask blank M to be measured, corrected or compensated. However, too many numbers of the fiducial marks 18 would make it difficult to calibrate the reference coordinates. In this embodiment, therefore, one fiducial mark 18 for each of two corners, totally two fiducial marks 18 are arranged.

Although not particularly limited to, the fiducial mark 18 has a planar size of, for example, 200 to 2000 nm. A method for forming the fiducial mark is not limited to the above one, for example, it is also possible to utilize a fiducial mark that is obtained by forming the multilayer film ML on a flat substrate surface and then irradiating the multilayer film ML with FIB or short-wavelength laser light. Further, adopting a method for optically detecting an edge position of the mask blank M can also achieve similar effects.

Next, a method for manufacturing a reflective mask will be explained below. An absorber pattern corresponding to an integrated circuit pattern is formed on the reflective mask blank M that has been inspected as described above. Conventionally, once a hard-to-repair defect has been detected, the mask blank is regarded as a defective, being put into disposal, even if the defect is a minute-sized one.

In this embodiment, even if various types of defects, such as convex defects or concave defects, are present in the mask blank M, those defects can be concealed by the absorber pattern, thereby reducing a defective fraction of the mask blank.

First, by using the above-described inspection method, positional information on defects of the mask blank M is stored in advance. In this case, the position coordinate of each defect can be precisely grasped by utilizing the above-described fiducial marks 18.

Subsequently, based on the stored defect positional information, a relative position between an absorber pattern mask and the mask blank for defining a forming position of the absorber pattern is determined. At this moment, the absorber pattern mask can be positioned, e.g., so as to conceal the defect. Then, based on the determined relative position, an absorber pattern is formed on the mask blank. In the resulting reflective exposure mask, the defect is concealed under the absorber pattern, therefore, there is no trouble in exposure projection of the mask pattern onto the semiconductor substrate.

As described above, the apparatus and the method for inspection of a mask blank according to this embodiment can easily determine surface irregularities that may cause phase defects of the mask blank, thereby analyzing factors of defect generation and facilitating development of technique for manufacturing defect-free mask blanks.

Further, since the position of a phase defect can be specifically determined, manipulating the positional relationship between the phase defect and the absorber pattern that defines the mask pattern of semiconductor circuits on the multilayer film can improve yield of reflective exposure masks in manufacturing. As a result, low-cost reflective exposure masks can be supplied.

Furthermore, during exposure process using the reflective exposure mask, considering the shifting amount of the absorber pattern in addition to the relative planar position of the mask and the wafer can facilitate patterns of the multilayered mask to be formed on the wafer with good alignment accuracy. As a result, this approach can improve performance, reliability and yield of semiconductor integrated circuits. In addition, cost reduction of the reflective exposure mask can promote cost reduction of semiconductor integrated circuits that requires high performance.

Embodiment 2

In this embodiment, exemplified here is a case where an optical branching element formed of a diffraction grating is used instead of the beam splitter BS in the inspection apparatus shown in FIG. 1.

Figure 8A:
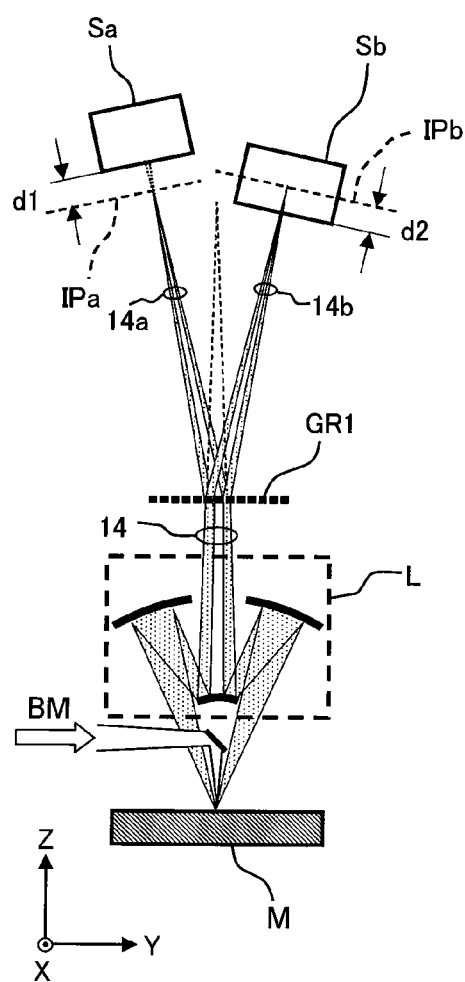
FIG. 8A is a configurative view showing an example in which a transmissive diffraction grating is used.
Figure 8B:
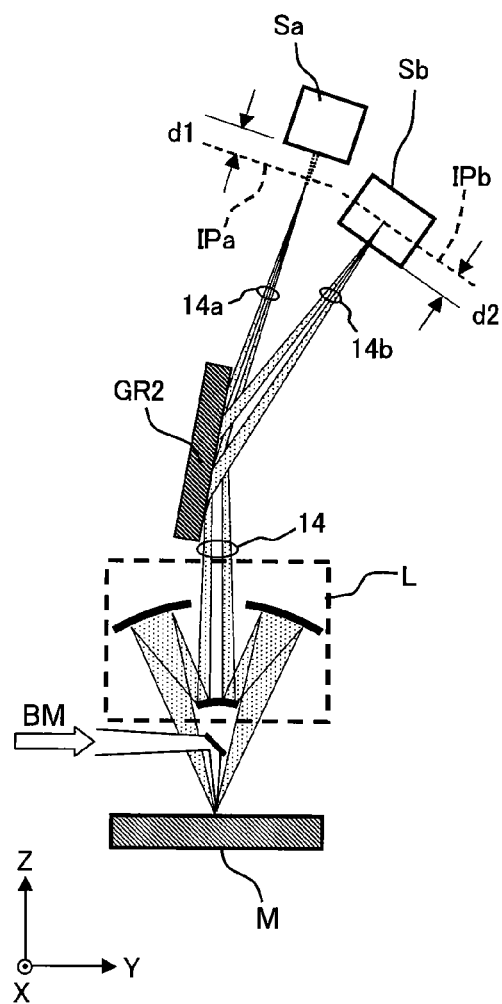
FIG. 8B is a configurative view showing an example in which a reflective diffraction grating is used.

FIG. 8A is a configurative view showing an example in which a transmissive diffraction grating GR1 is used. FIG. 8B is a configurative view showing an example in which a reflective diffraction grating GR2 is used. Components other than the optical branching element are similar to those of FIG. 1, and their redundant description is omitted.

In FIG. 8A, the diffraction grating GR1 is composed as a stencil transmissive diffraction grating, for example, with a group of linear openings having a pitch of 140 nm. As the light beam 14 outputted from the imaging optical system L passes through the diffraction grating GR1, the light beam may branch into several-order diffracted light according to a diffraction angle which can be determined by grating pitch and wavelength of light. Among the resulting diffracted light, +1st order diffracted light can be utilized for the light beam 14a, and −1st order diffracted light can be used for the light beam 14b.

In FIG. 8B, the diffraction grating GR2 is composed as a reflective diffraction grating, and an average incident angle of the light beam 14 is set at, e.g., 80 degrees. The light beam 14 outputted from the imaging optical system L enters the diffraction grating GR2 to branch into several-order diffracted light according to a diffraction angle which can be determined by grating pitch and wavelength of light. Among the resulting diffracted light, +1st order diffracted light can be utilized for the light beam 14a, and −1st order diffracted light can be utilized for the light beam 14b.

In either case, the 2D array sensor Sa is located for detecting a positively defocused image, at a position which is displaced by a predetermined distance d1 from the focal plane IPa of the light beam 14a along the light traveling direction. On the other hand, the 2D array sensor Sb is located for detecting a negatively defocused image, at a position which is displaced by a predetermined distance d2 from the focal plane IPb of the light beam 14b along a direction opposite to the light traveling direction. This arrangement can keep the distance between the sensors Sa and Sb at about few centimeters. Incidentally, in a case where there is a room between the 2D array sensors Sa and Sb, zero-order diffracted light may be captured by one of the 2D array sensors Sa and Sb in place of one of the +1st and −1st order diffracted light.

In a case the light beams 14a and 14b branched by the diffraction gratings GR1 and GR2 differ in intensity from each other, sensitivities of the 2D array sensors Sa and Sb are preferably calibrated in correspondence to ratio of intensities of the light beams 14a and 14b, thereby obtaining the outputs of the same level.

This embodiment has an advantage that a rigid diffraction grating can be used without using a difficult-to-manufacture multilayer film beam splitter. Also, since the two sensors Sa and Sb can be located close to each other, there is another advantage that the optical system is well balanced with respect to the center of gravity, as compared with the arrangement of FIG. 1, being less susceptible to vibrations due to scanning of the stage 2.

Furthermore, it is needless to say, as in Embodiment 1, that concave and convex configurations of phase defects can be determined, that coordinates of a detected defect can be measured and that, if desired, defect coordinates information can be considered during formation of the absorber pattern.

Embodiment 3

In this embodiment, described below are a method for reflective exposure using the above-described reflective exposure mask, as well as a method for manufacturing semiconductor integrated circuits.

Figure 9:
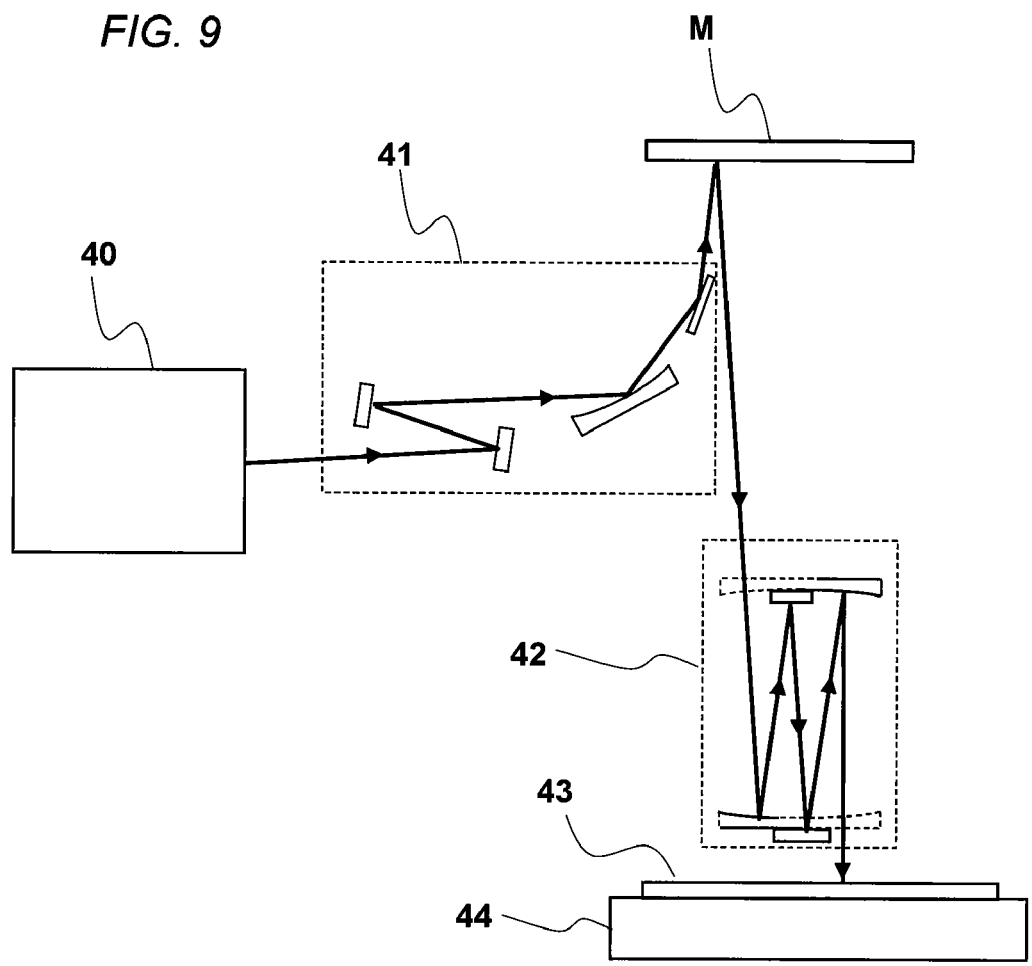
FIG. 9 is a configurative view showing an example of a reflective exposure apparatus.

FIG. 9 is a configurative view showing an example of a reflective exposure apparatus. A mask M is manufactured according to the above-described mask manufacturing method. EUV light having a center wavelength of 13.5 nm emitted from a light source 40 illuminates a pattern surface of the mask M via an illumination optical system 41 composed of a plurality of multilayer-film reflecting mirrors. Light reflected from the pattern surface passes through a reduction-projection optics 42 (having a magnification of, e.g., ¼) composed of a plurality of multilayer-film reflecting mirrors to be focused onto a wafer 43. The wafer 43 is mounted on an in-plane movable stage 44. A pattern corresponding to the mask M is transferred to a desired region of the wafer 43 by repetition of movement of the stage 44 and pattern exposure.

FIGS. 10A to 10F are cross-sectional views for explaining an example of a method for manufacturing semiconductor integrated circuits. Illustrated here is a case of manufacturing semiconductor integrated circuits having a twin-well type CMIS (Complimentary MIS) circuit, but the present invention can be also applied to other various types of circuits.

A substrate 103s constituting a semiconductor wafer 103 is formed of, for example, generally disc-shaped n⁻-type Si (silicon) single crystal. In an upper portion of the substrate 103s are formed, for example, an n-well 106n and a p-well 106p (see FIG. 10B). In the n-well 106n, for example, n-type impurity of P (phosphorus) or As (arsenic) is introduced. Also, in the p-well 106p, for example, p-type impurity of B (boron) is introduced. The n-well and the p-well can be formed through the following steps.

First, a wafer alignment mark for mask alignment is formed on the semiconductor substrate 103s (not shown). This wafer alignment mark may also be formed in the well formation process by adding a selective oxidation step.

Figure 10A:
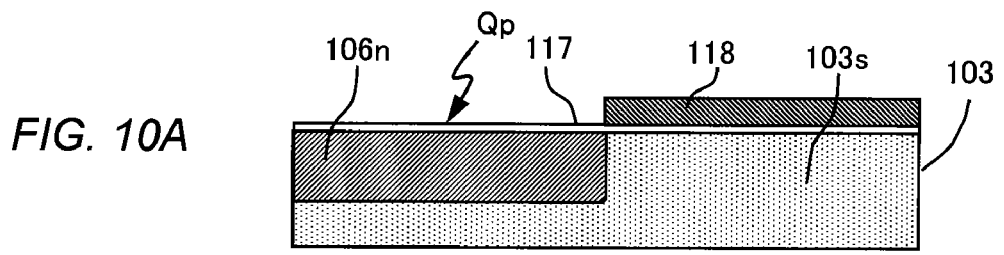
FIG. 10A to 10F are cross-sectional views for explaining an example of a method for manufacturing semiconductor integrated circuits.

Subsequently, as shown in FIG. 10A, an oxide film 117 is formed on the substrate 103s, and then a resist pattern 118 for ion-implantation masking is formed on the oxide film 117 using ordinary optical lithography. Thereafter, P (phosphorus) or As is ion-implanted, resulting in the n-type well 106n.

Figure 10B:
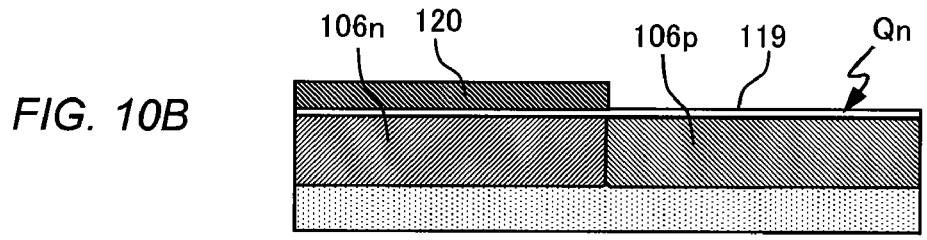

Next, the resist pattern 118 is removed by ashing process, and then the oxide film 117 is also removed, and then an oxide film 119 is formed on the substrate 103s as shown in FIG. 10B. Then, a resist pattern 120 for ion-implantation masking is formed on the oxide film 119 using ordinary optical lithography. Thereafter, B (boron) is ion-implanted, resulting in the p-type well 106p.

Figure 10C:
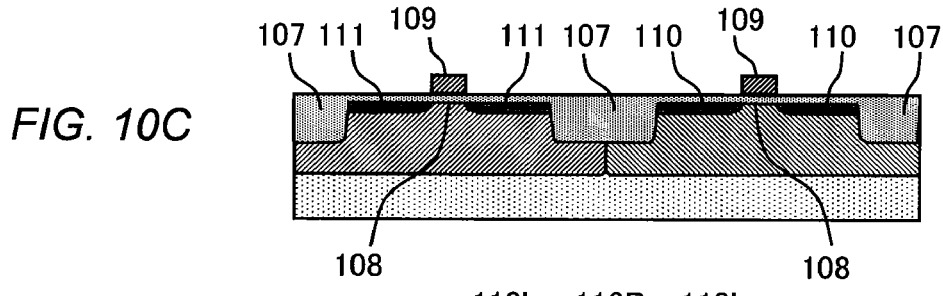

Next, the resist pattern 120 is removed by ashing process, and then the oxide film 119a is also removed, and then, as shown in FIG. 10C, a field insulating film 107 for isolation is formed of, e.g., silicon oxide in a grooved isolation configuration on the upper principal surface of the substrate 103s.

This isolation configuration has a minimum size, for example, as small as 36 nm on the wafer, its dimensional accuracy requirement being as strict as 3.5 nm. Therefore, EUV lithography can be used for the lithography for fabrication of this isolation.

In an active region surrounded by the field insulating film 107, an n-MIS transistor Qn and a p-MIS transistor Qp is formed. A gate insulating film 108 of each transistor is made of, for example, silicon oxide using thermal oxidation process or the like.

Also, a gate electrode 109 of each transistor has a minimum size, for example, as small as 32 nm on the wafer, its dimensional accuracy requirement being as strict as 3 nm. Accordingly, a gate-forming film of low-resistivity polysilicon is deposited using, e.g., CVD process, and then a resist pattern is formed using EUV lithography, and then the gate electrode 109 is formed using etching process. The lithography in this step is generally referred to as gate-layer lithography, for which pattern transfer with extremely fine and high accuracy of dimension is required.

A semiconductor region 110 of the n-MIS transistor Qn is formed in a self-aligned manner with respect to the gate electrode 109 by introducing, for example, P (phosphorus) or As into the substrate 103s with the gate electrode 109 used as a mask using ion implantation process or the like. Also, a semiconductor region 111 of the p-MIS transistor Qp is formed in a self-aligned manner with respect to the gate electrode 109 by introducing, for example, B (boron) into the substrate 103s with the gate electrode 109 used as a mask using ion implantation process or the like.

In this case, the gate electrode 109 may be formed of various materials, not limited to formation of a single film of low-resistivity polysilicon. For instance, the gate electrode 109 may be provided in a so-called polycide structure having a silicide layer of tungsten silicide, cobalt silicide, etc, on a low-resistivity polysilicon film. Alternatively, the gate electrode 109 may also be provided in a so-called polymetal structure in which a barrier conductor film of titanium nitride, tungsten nitride, etc, is interposed on a low-resistivity polysilicon film and thereover a metal film of tungsten or the like is formed.

Figure 10D:
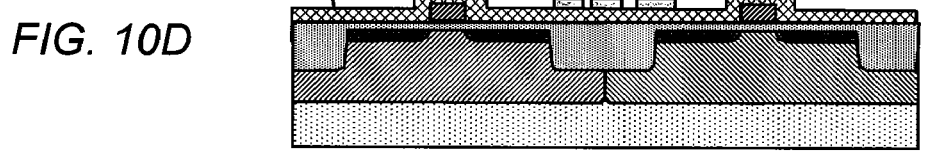

Next, as shown in FIG. 10D, an interlayer insulating film 112 of silicon oxide is deposited on the substrate 103s using, e.g., CVD process, and then a polysilicon film for interconnection is deposited on top of the interlayer insulating film 112 using CVD process or the like. Subsequently, lithography is carried out on the polysilicon film, and then patterned by etching, and thereafter impurities are introduced to specified regions of the patterned polysilicon film, resulting in interconnections 113L and a resistor 113R made of polysilicon film.

Figure 10E:
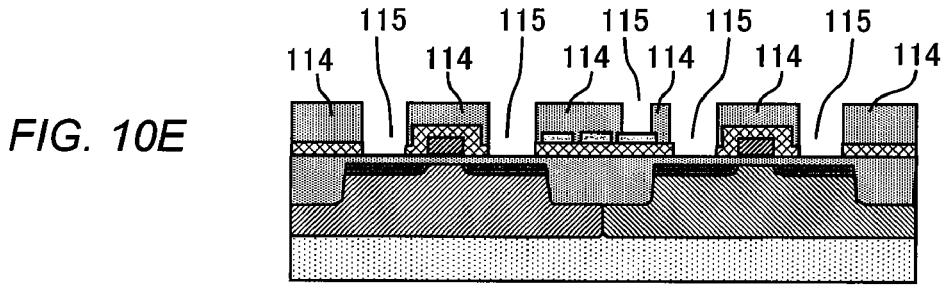

Next, as shown in FIG. 10E, a silicon oxide film 114 is deposited on the substrate 103s using, e.g., CVD process. Then, a resist pattern is formed using EUV lithography for the interlayer insulating film 112 and the silicon oxide film 114, and then contact holes 115 are formed using etching process to partially expose the semiconductor regions 110 and 111 and the interconnection 113L. Since fine holes are difficult to resolve due to effects of optical diffraction, an EUV lithography technique having a high resolution can be applied to this lithography for forming contact holes.

Figure 10F:
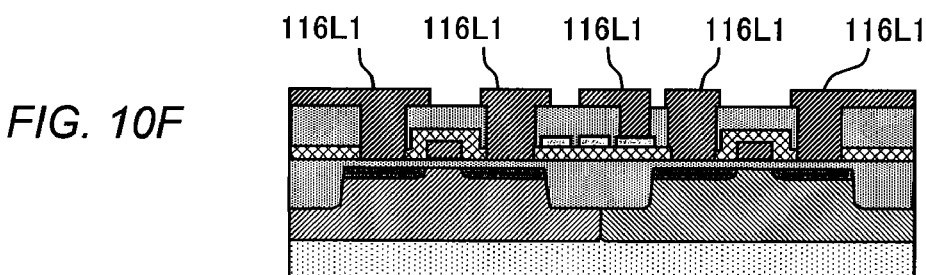

Next, as shown in FIG. 10F, metal films made of Ti (titanium), TiN and W (tungsten) are sequentially deposited on the substrate 103s using, e.g., sputtering process or CVD process, and thereafter a resist pattern is formed on the metal films using EUV lithography, and then a first interconnect layer 116L1 is formed by etching process. The first interconnect layer 116L1 includes fine dense patterns and isolated patterns, and involves complicated layout configurations for detouring of interconnections behind the neighboring interconnections or connecting of interconnections. Accordingly, the lithography for the first interconnect layer also requires high resolution and accuracy of dimension.

Subsequently, alike as the first interconnect layer 116L1, a second interconnect layer (not shown) can be also formed, thereby manufacturing a final product.

Among a series of manufacturing steps for the semiconductor device as described above, the lithography for the gate layer, the contact holes and first interconnect layer require sufficiently higher resolution performance, therefore, EUV lithography is preferably applied thereto.

Further, for the masks for the gate layer and the first interconnect layer, it is preferable to employ a defect-free mask that has been proved in a state of mask blank, which can be inspected by means of such inspection apparatus and method as described in Embodiments 1 and 2.

Also, for the mask for the contact hole, it is preferable to employ a mask that has been proved to have no defect in vicinities of the contact hole in a state of mask blank, which can be inspected by means of such inspection apparatus and method as described in Embodiments 1 and 2.

The contact hole has a small area with a pattern density as low as 5%, hence, there is little possibility that defects occur in vicinities of the contact hole, thereby enhancing yield of the mask blank available by this method. As a result, the yield of semiconductor integrated circuits fabricated according to this embodiment is likely to become higher than those fabricated through the conventional method for defect inspection of a mask blank.

As described above, by employing a mask that has been proved to have no defect in a state of mask blank, which can be inspected by means of such inspection apparatus and method as described in Embodiments 1 and 2, pattern transfer can be implemented using a highly reliable mask. As a result, performance, reliability and yield of manufactured semiconductor integrated circuits can be improved, thereby contributing to cost reduction of the semiconductor integrated circuits.

Although the present invention has been described in detail in conjunction with preferred embodiments thereof, the invention is not limited only to the above-described embodiments, and it is needless to say that various changes and modifications may be made without departing from the scope of the present invention.

The present invention is industrially useful in that semiconductor devices including fine and highly accurate patterns can be manufactured at high production efficiency.

What is claimed is:

1. An apparatus for inspection of a mask blank, comprising:
   a stage for mounting a reflective mask blank to be inspected;
   a light source for generating inspection light including the same wavelength as used during mask exposure by means of a mask having patterns formed on the reflective mask blank;
   an illuminating optics for illuminating a target region on the mask blank with the inspection light supplied from the light source;
   a dark-field imaging optics for collecting scattered light other than specularly reflected light out of light reflected from the target region to form a magnified image on a predetermined focal plane;
   an optical branching element for dividing light outputted from the dark-field imaging optics into a first and second light beams;
   a first image sensor having a plurality of detection pixels, the sensor being located at a position displaced by a predetermined distance from a focal plane of the first light beam along the light traveling direction;
   a second image sensor having a plurality of detection pixels, the sensor being located at a position displaced by a predetermined distance from a focal plane of the second light beam along a direction opposite to the light traveling direction; and
   an image processing unit for determining presence or absence of any defects in the mask blank, based on signals from the first and the second image sensors.

2. The apparatus according to claim 1, wherein the optical branching element is composed of a multilayer film.

3. The apparatus according to claim 1, wherein the optical branching element is composed of a transmissive diffraction grating.

4. The apparatus according to claim 1, wherein the optical branching element is composed of a reflective diffraction grating.

5. The apparatus according to claim 1, further comprising a stage drive unit for in-plane movement of the stage;
   wherein the first and the second image sensors are image sensors capable of Time Delayed Integration operations in synchronization with continuous movement of the stage.

6. The apparatus according to claim 1, wherein the light source generates the inspection light including an extreme ultraviolet wavelength.

7. A method for inspection of a mask blank, including steps of:
   irradiating a reflective mask blank to be inspected with inspection light to illuminate a target region, the inspection light including the same wavelength as used during mask exposure by means of a mask having patterns formed on the reflective mask blank;
   collecting scattered light other than specularly reflected light out of light reflected from the target region, and then dividing the collected light into a first and a second light beams to measure intensity distributions of respective inspection images formed by the first and the second light beams, respectively, by using a first and a second image sensors; the first image sensor being located at a position displaced by a predetermined distance from a focal plane of the first light beam along the light traveling direction; the second image sensor being located at a position displaced by a predetermined distance from a focal plane of the second light beam along a direction opposite to the light traveling direction; and determining presence or absence of any defects in the mask blank, based on signals from the first and the second image sensors.

8. The method according to claim 7, wherein the step of determining presence or absence of defects includes steps of:

comparing the signal of the first image sensor with a preset first threshold;

comparing the signal of the second image sensor with a preset second threshold; and comparing the signal of the first image sensor with the signal of the second image sensor;

wherein convex defects and concave defects of the surface configuration are discriminated based on the result of each comparison.

9. A method for manufacturing a reflective exposure mask by forming an absorber pattern on a reflective mask blank, including steps of;

inspecting defects of the mask blank using the method for inspection of a mask blank according to claim 7 or 8;

storing positional information on the defect;

determining a relative position between an absorber pattern mask and the mask blank for defining a forming position of the absorber pattern, based on the stored defect positional information on the defect; and forming the absorber pattern on the mask blank, based on the determined relative position.

10. A method for reflective exposure, including steps of:

mounting on a reflective exposure apparatus a mask which is obtained using the method for manufacturing a reflective exposure mask according to claim 9, and projecting the absorber pattern in a reduced size onto a semiconductor substrate.

11. A method for manufacturing semiconductor integrated circuits, wherein an integrated circuit pattern is formed on a semiconductor substrate using the method for reflective exposure according to claim 10.

* * * * *